United States Patent [19]

Livingston

[11] 4,335,040

[45] Jun. 15, 1982

[54] THERAPEUTIC PRODUCT AND METHOD

[75] Inventor: William S. Livingston, Woodland Hills, Calif.

[73] Assignee: Livingston Labs., Van Nuys, Calif.

[21] Appl. No.: 775,225

[22] Filed: Mar. 7, 1977

Related U.S. Application Data

[63] Continuation of Ser. No. 583,724, Jun. 4, 1975, abandoned, which is a continuation-in-part of Ser. No. 602,434, Oct. 6, 1966, Pat. No. 3,526,697, which is a continuation-in-part of Ser. No. 207,146, Jun. 26, 1962, abandoned, which is a continuation-in-part of Ser. No. 660,559, May 21, 1957, abandoned, and Ser. No. 655,320, Apr. 26, 1957, abandoned, which is a continuation-in-part of Ser. No. 623,711, Nov. 21, 1956, abandoned, which is a continuation-in-part of Ser. No. 256,334, Nov. 14, 1951, abandoned, which is a continuation-in-part of Ser. No. 127,799, Nov. 16, 1949, abandoned.

[51] Int. Cl.$^3$ .................... A61K 35/12; A61K 35/50; C07G 7/00

[52] U.S. Cl. ................................. 260/112 R; 424/95; 424/105

[58] Field of Search .................... 260/112 R, 373, 787

[56] References Cited

U.S. PATENT DOCUMENTS

| | | | |
|---|---|---|---|
| 1,171,299 | 2/1916 | Archibald | 424/101 |
| 1,216,046 | 2/1917 | Archibald | 424/95 |
| 1,517,845 | 12/1924 | Larson | 424/92 |
| 1,882,112 | 10/1932 | Boidin | 195/79 |

FOREIGN PATENT DOCUMENTS 679738  9/1952  United Kingdom .

OTHER PUBLICATIONS

Journal of the National Cancer Institute, vol. 23, Sep. 1959, pp. 587-603, Livingston et al.
Stolper-Wiener Klinische Woehenshrift 44:272-3 (1931).
Chambers, Lancet, vol. 1, 1926, p. 1170.
Donner Foundation "Index to the Literature of Experimental Cancer Research" 1900-1935, 1948, pp. 357-359, 409-412, 500-505, 787-788, 803-806.
Zinsser, "Infection & Resistance 2nd ed. 1918, MacMillan Co. N.Y. pp. 65-66.

*Primary Examiner*—Howard E. Schain
*Attorney, Agent, or Firm*—Thomas D. Kiley

[57] ABSTRACT

Described herein are compositions obtained in accordance with the procedure which comprises placing in a pressure vessel a quantity of material comprising animal tissue selected from the group consisting of fresh human placenta or other animal tissues, enclosing and sealing the pressure vessel, maintaining the temperature within the vessel between about 5° C. and less than 60° C. and the pressure greater than about 15 psig and less than about 45 psig over a period from about 2 weeks to about 1 year, opening the vessel at the conclusion of that period and recovering and sterilizing a liquid portion of the semiliquid contents of the vessel. Preferably, the material is maintained in the vessel at a temperature from about 35° C. to about 55° C. and a pressure from about 23 psig to about 37 psig for a period from about 3 to about 4 months. The recovered, sterilized portion can be immediately employed or lyophilized and subsequently reconstituted with, e.g., sterile saline for employment as a therapeutically active agent in the treatment of rheumatoid arthritic and osteoarthritic subjects and for regression of spontaneous benign and malignant neoplasms in mammalian subjects.

10 Claims, 2 Drawing Figures

THERAPEUTIC PRODUCT AND METHOD

CROSS-REFERENCE TO RELATED APPLICATIONS

This is a continuation, of application Ser. No. 583,724 filed June 4, 1975, which is a continuation-in-part of my copending application Ser. No. 602,434, filed Oct. 6, 1966 (U.S. Pat. No. 3,526,697, issued Sept. 1, 1970), which was a continuation-in-part of my application Ser. No. 207,146, filed June 26, 1962, which was a continuation-in-part of my application Ser. No. 660,559, filed May 21, 1957, and Ser. No. 655,320, filed Apr. 26, 1957, which, in turn, was a continuation-in-part of my application Ser. No. 623,711, filed Nov. 21, 1956, that being a continuation-in-part of my application Ser. No. 256,334, filed Nov. 14, 1951, which, in turn, was a continuation-in-part of my application Ser. No. 127,799, filed Nov. 16, 1949, all applications saving that first mentioned now being abandoned.

FIELD OF THE INVENTION

This invention relates to a composition and the process for the production thereof, which composition is effective against arthritis and exhibits tumor growth inhibitory action.

BACKGROUND OF THE INVENTION

The general background relating to the present invention is set forth in Livingston et al, "The Treatment of Spontaneous Tumors of the Dog and Cat with a Filtrate from a Tissue Lysate", *Journal of the National Cancer Institute,* Volume 20, No. 2, February, 1958; Lamson et al, "Growth Inhibition of Transplantable Mouse Lymphosarcoma by a Filtrate from Placental Lysates", *Journal of the National Cancer Institute,* Volume 23, No. 3 (1959); and Maxson et al, "Controlled Study of a New Antiarthritic Substance", *Annals of Allergy,* Volume 27, No. 2, February, 1969—all of which are incorporated herein by reference.

BRIEF SUMMARY OF THE INVENTION

According to this invention, there is provided a process and a composition produced by a process which comprises autolysis of fresh human placenta or other normal or malignant animal tissues at temperatures from about 5° C. to less than about 60° C. and pressure greater than about 15 psig but less than about 45 psig over a period from about 2 weeks to about 1 year followed by the recovery and sterilization of a liquid portion of the semi-liquid materials resulting from autolysis.

One object of this invention is to provide a therapeutically active substance by the prolonged autolysis of animal tissue at super atmospheric pressures.

This and other objects and advantages of the invention will become apparent from the detailed description which follows and from the accompanying drawings in which:

FIG. 1 is a perspective view illustrating a typical apparatus suitable for carrying out the process of this invention; and FIG. 2 is a vertical sectional view taken on the line 2—2 of FIG. 1.

DETAILED DESCRIPTION OF THE INVENTION

Figures 1, 2:
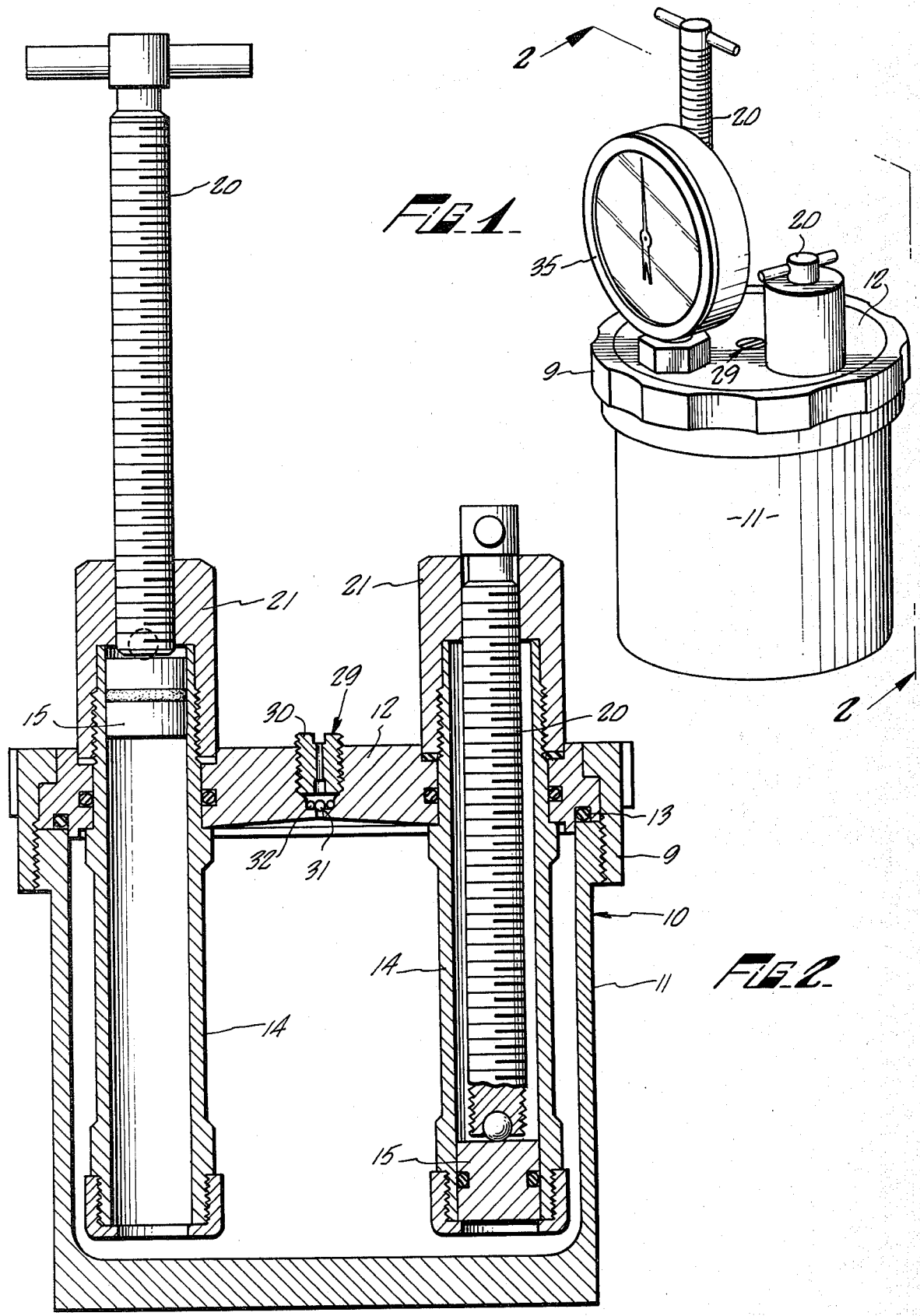

Investigators have suggested that the neoplastic diseases as well as the systemic rheumatic diseases are autoimmune diseases. Tissue cells such as those within living mammalian organisms die and undergo autolysis constantly, and the evidence suggests that the death and lysis of cells during embryological development influence the orderly development of the embryo, just as lysis products are believed to influence the chemical processes of all living organisms. While the method by which the autolysate of this invention achieves its effectiveness has not yet been completely established, and while I do not wish to be bound by any particular theory, studies which have been conducted suggest that some of the products of cell autolysis stimulate organisms into producing blocking or inhibiting antibodies which inactivate or neutralize the autoimmune mechanism. Thus, the efficacy of the composition of this invention may result from the influence lysis products on the autoimmune mechanism.

The "animal tissue" referred to herein as subjected to autolysis is any normal or malignant tissue of mammalian animals, including man, removed either surgically or at postmortem, and includes without limitation glandular tissue, e.g., thyroid or pituitary tissue. Preferably, the animal tissue employed is less vascular than liver, and most preferably is tissue rich in hormones, such as follicular stimulating hormone and chorionic gonadotropin, e.g., neoplastic and neoplastic-related tissue such as testes, ovaries, and placenta. Fresh human placenta is the preferred tissue candidate for autolysis.

Preferably, although not necessarily, autolysis is conducted in the presence of antibacterial agents such as penicillin, chloromycetin, streptomycin, sulfathiazole, sulfasuccidine, and sulfamerezine, and/or antifungal agents such as griseofolvin.

The drawings illustrate an apparatus suitable for carrying out the autolytic process of the invention. The apparatus comprises a pressure vessel 10, preferably of stainless steel. The vessel includes a generally cylindrical body 11 of about 750 cc. capacity, closed at the bottom and having an open top to which is affixed, by means of a threaded ring 9, a cover member 12 provided with a suitable seal 13. A pair of cylinders 14 are carried by the cover member and extend downwardly into the interior of the body 11, each of the cylinders being provided with a piston 15 adapted to be raised and lowered within the cylinders by means of screw members 20 threadedly engaged in cap members 21 fitted on the upper ends of the cylinders.

Means are provided for releasing the pressure within the vessel and, as shown in the drawing, these means may include a valve 29 comprising a plug member 30 threadedly engaged in a central opening in the cover member 12, the plug member in the closed portion shown forcing a ball 31 against its seat 32. A pressure gauge 35 is inserted into the cover member to complete the assembly.

Prior to autolysis, tissue is preferably ground and adjusted by the addition of physiological saline and base, e.g., 0.5 N NaOH to a standard pH. Preferably, the feed to autolysis is adjusted to a pH of about 7.8. Current practice, then, with reference to the preferred tissue—human placenta—is to combine ground placenta and saline in the proportion of about 300 cc. saline to about 700 gm. placenta, followed by pH adjustment to 7.8.

Autolysis is preferably conducted in the substantial absence of oxygen. Accordingly, a pressure vessel is filled with the tissue-saline mixture and air removed by evacuation. Removed air is preferably replaced by a gas providing a reducing atmosphere such as hydrogen, methyl mercaptan, methane, or other hydrocarbon gases. Where autolysis is commenced under aerobic conditions resulting from residual air in the pressure vessel, facultative anaerobes contained in the non-sterile tissue employed appear to reduce oxygen content to acceptable levels. Ultimately in the preferred embodiment, of course, those microorganisms are eliminated by antibacterial agents added to the pressure vessel with the tissue-saline mixture.

Like most chemical reactions, the autolysis reaction which provides the active ingredient of the composition of this invention appears to be time and temperature dependent. Active fractions have been secured after autolysis of as little as two weeks, although 6 weeks is more preferred and a period of autolysis from about 3 months to about 4 months is most preferred. Wile maximum yield of active therapeutic substance is obtained from the periods last-mentioned, longer periods of up to 12 months have neither increased nor decreased the product potency.

Autolysis is conducted at temperatures ranging from about 5° C. to less than about 60° C. Preferably, temperatures maintained at from about 35° C. to about 55° C., most preferably from about 40° C. to about 47° C. Of course, because the autolysis reaction is time-temperature dependent, lowering temperature will require longer residence time to achieve equivalent activity.

The most critical parameter of autolysis appears to be pressure, which must be maintained at greater than about 15 psig but less than about 45 psig. Preferably, pressure is maintained at from about 23 psig to about 37 psig, most preferably from about 25 psig to about 35 psig. At pressures less than 15 psig or greater than 45 psig, no active fraction has been obtained to date.

Following the completion of autolysis, the pressure vessel is opened and a liquid portion recovered from the semi-liquid contents of the vessel, as by filtration or centrifugation. Preferably, the recovered liquid portion is then sterilized, as by passage through a sterilizing filter. Preferably, prior to recovering the liquid portion from the raw autolysis product, the raw product is boiled to coagulate contained liquid, heat-unstable protein. Where boiling of the raw product is effected, pH should be adjusted by the addition of base, e.g., 0.5 N NaOH, to between about 6.5 and 7.5, preferably to about 7.3-7.4. Below about pH 6.5 or above about pH 7.5, boiling is believed to adversely influence activity of the autolysate. Of course, the product can be refined by means other than boiling, e.g., starch block electrophoresis or column electrophoresis with ion exchange resins.

The sterilized liquid product is preferably stored in 1-cc. quantities, which may be lyophilized for storage and subsequently reconstituted by the addition of physiological saline or the like.

Preferred compositions produced according to the invention exhibit total nitrogen content ranging from about 8.0 mg/ml to about 16.5 mg/ml; and non-protein nitrogen ranging from about 6.5 mg/ml to about 14.0 mg/ml. The product contains from about 6.0% to about 13.0% nucleic acids, as determined by the Orinol Method. The product exhibits an ultraviolet absorptivity coefficient at 262 millimicrons of from about 11.0 to about 22.0 od, and at 278 millimicrons, from about 11.0 to about 20.0 od—a very small peak believed attributable to the presence of hormones freed from tissue during autolysis is observed at 195 millimicrons. Absorbance data was taken in water at a concentration of 1% by weight liquid filtrate.

Electrophoresis of the liquid filtrate indicates that it comprises three principal fractions as follows:

TABLE I

| FRACTION: | 1 | 2 | 3 |
|---|---|---|---|
| % wt (range): | 15–20 | 65–80 | 5–8 |
| Mobility corresponding to: | Gamma globulin | $a_1$, $a_2$ globulins | (beyond) human serum albumin |

The invention is further illustrated by reference to the following examples in which all parts are by weight unless otherwise specified:

EXAMPLE 1

Fresh human placentas were obtained in a sterile metal container from the delivery room using ordinary sterile precautions. No antibacterial preservatives were added. The placenta was ground in a meat grinder and 500 grams placed in the pressure vessel with 150 cc of 0.9% sterile saline. The cover member of the vessel was then put into place and sealed. The internal pressure was then regulated to 25 psig by lowering the pistons 15 by means of the screw members 20, and the entire vessel and contents placed in a hot air incubator at 40° C.

During the entire period of incubation the internal pressure was maintained at 25 psig. Upon the evolution of gases, the screw members were gradually raised to maintain the pressure equilibrium. After about 72 hours, sufficient gas had evolved to require release thereof by opening of the valve 29. Sufficient gas was released to bring the pressure below 25 pounds, and the pressure again brought back to that value by adjustment of the pistons 15. Pressure adjustments in this manner were made every one-half hour during the waking period and at four-hour intervals during the night.

Autolysis in this manner was continued for three months, at which time the vessel was opened. The contents were extremely odiferous, cream-like in consistency, and had the color of port wine. The pH was found to be 6.8.

The semi-liquid raw product was strained through unbleached muslin previously washed to remove sizing. The liquid was then passed through coarse filter paper (Aloe 42,700) four times through the same sheet to produce a clear filtrate. The liquid was then sterilized by filtration through a 100 cc Seitz filter flash using type St-3, size L-6 filter pads, with a porosity of 0.1. Approximately 450 cc of filtrate was obtained. This filtrate was then drawn through sterile tubing into previously evacuated sterile rubber capped bottles and was ready for use. Storage of the product in a cold room at 3° C. will preserve it for periods of a week or longer.

EXAMPLE 2

Fresh human placentas were obtained in a sterile metal container from the delivery room using ordinary sterile precautions. The placentas were ground in a meat grinder and 500 grams thereof placed in the pressure vessel with 200 cc of 0.9% sterile saline, 310,000 units of penicillin, 0.210 grams of streptomycin and 0.310 grams of chloromycetin. The pH of the admixture was adjusted to 7.8 with 5 N NaOH and the admixture was equilibrated for about 1 hour. The pH was readjusted to 7.8 and equilibrated in this manner twice more, whereupon the vessel was covered and sealed. The vessel was provided with an adapter (not shown), comprising a threaded tube replacing the valve 29, the tube being threaded into the central opening in the cover 12 and extending outwardly therefrom. A rubber tubing (not shown) is affixed to the end of the tube and provided with suitable clamps (not shown).

The sealed vessel was turned upside down and shaken to transfer all air out of the cylinders and into the space between the level of the admixture and the inverted bottom of the vessel, whereupon the air was evacuated by attaching a vacuum pump inlet line (not shown) to the tube by means of the rubber tubing described above. The inverting, shaking, and evacuation steps were done twice and then hydrogen gas was introduced through the rubber tubing and tube until the pressure on the gauge was about 27 psig. The rubber tubing was then clamped off and the vessel and contents placed in a hot air incubator at a temperature of 47° C. After a short time at this temperature, the gauge pressure rose to 35 psig. Incubation was carried on for six weeks, during which it was necessary every week to regulate the pressure to maintain it at 33-35 psig by inward adjustment of the pistons 15.

After incubation as described, the vessel was opened, the product therein being a dark red in color, with little or no odor, partly liquified but containing a considerable quantity of solids, and having a pH of 6.6.

The pH was adjusted to 7.4 by the slow addition of 5 N NaOH with stirring and the admixture was boiled in a stainless steel pan over an open flame for about 10 minutes. The pH of the cooled admixture was 7.6; it was dark brown in color and it had a considerably increased solids content due to coagulation of liquid, heat unstable proteins during the boiling step. The admixture was clarified and filtered as in Example 1 and was then lyophilized and stored ready for reconstitution and use.

EXAMPLE 3

The process of this example was substantially identical to that of Example 1 except that horse sarcoma was substituted for the placenta as the raw material.

EXAMPLE 4

The process of this example was substantially identical to that of Example 1 except that here the process was carried out under anaerobic conditions. In this connection, the saline was boiled to remove oxygen and then cooled prior to introduction into the pressure vessel. After filling, the pressure vessel was rotated in such a way as to release all air from the cylinders 14 and to cause the air to travel toward the valve 29. The plug 30 and the ball 31 were then removed and all air replaced with boiled saline added by means of a syringe.

EXAMPLE 5

Fresh human placentas were obtained in a sterile metal container from the delivery room, using sterile precautions, and ground in a sterilized meat grinder. 500 grams of the ground material was placed in the pressure vessel with 150 cc of 0.9% sterile saline. To this was added 10 cc of toluene and the vessel contents were thoroughly mixed. The cover member of the vessel was then put into place and sealed. The plug member 30 and ball 31 were then removed and additional saline injected into the vessel with a syringe to displace the air trapped between the vessel contents and the cover member. The ball and plug member were then replaced, leaving about 40 cc of air trapped in the cylinders 14.

The internal pressure in the vessel was then regulated to 25 psig by lowering the pistons 15 by means of the screw members, and the entire vessel and contents placed in a hot air incubator at 40° C.

During the entire period of autolysis, the internal pressure was maintained at 25 psig, any deviations in internal pressure being compensated for by gradual adjustment of the screw members to maintain the pressure equilibrium.

Autolysis in this manner was continued for three months, at which time the vessel was opened. The product, cream-like in consistency and having a pH of 6.8, was separated into a liquid and a solid phase by centrifugation and the liquid phase passed through a sterilizing Sietz filter, the filtrate comprising the final product.

As will appear from the foregoing examples, anti-bacterials (when used) can be employed in combination. Alternatively, as shown by the examples, aseptic conditions can be achieved within the pressure vessel by the employment of preservatives such as chloroform, toluene, or other suitable aromatic compounds or combinations thereof. When operating without anti-bacterial agents or preservatives, the chance bacterial contamination inevitably present in the tissue raw material results in some evolution of gas requiring appropriate adjustments to maintain the pressure substantially constant at the desired level.

The product produced by the process of this invention has been discovered to exhibit therapeutically active properties in the regression of spontaneous benign and malignant neoplasms, and in the treatment of osteoarthritis and rheumatoid arthritis. Treatment is by injection in either case, intracutaneous injection being the preferred course.

Optimal dosage will vary from one subject to another and is best determined by the administering physician. In double blind studies conducted with osteoarthritic and rheumatoid arthritic subjects, each subject was begun with injections of 0.1 ml of a one:one thousand dilution twice weekly. That dose was maintained where the patient showed improvement. Absent response to the drug, twice-weekly dosage of 0.1 ml of one:five hundred dilution was employed. That dosage was then increased by increments (one:one hundred, one:ten, etc.) to 0.1 ml of one:one (stock) solution. If 24 hours after the injection an arthritic patient experiences increased pain which subsides before the next injection is due, the dosage is high and should be decreased slightly (e.g., 0.01 to 0.05 dilution).

In humans, dosage levels of as high as 200 cc per day have been employed without any observed adverse effect. Dogs have tolerated from 0.18 cc to 0.67 cc of the filtrate per pound of body weight per day without adverse reaction, and larger doses have been tolerated by cats, one cat tolerating a maximum dose of 1.1 cc per pound body weight without adverse reaction. A large number of healthy adult mice have tolerated 2.00 cc given intraperitoneally daily for many weeks.

I claim:

1. A method for the production of a therapeutically active substance which comprises:
   (a) Placing in a pressure vessel a quantity of material comprising animal tissues selected from the group consisting of fresh human placenta or other normal or malignant animal tissues;
   (b) Enclosing and sealing said pressure vessel;

(c) Maintaining the temperature within said vessel from about 5° C. to less than about 65° C., and the pressure within said vessel greater than about 15 psig but less than about 45 psig for at least about 2 weeks;

(d) Opening said vessel at the conclusion of said period;

(e) Recovering a liquid portion of the semi-liquid contents of said vessel; and (f) Sterilizing the said liquid portion.

2. The method of claim 1 wherein said temperature is maintained between about 35° C. and about 55° C., and wherein said pressure is maintained between about 23 psig and about 35 psig.

3. The method of claim 1 wherein said temperature and said pressure are maintained in said vessel over a period from about 6 weeks to about 4 months.

4. The method of claim 2 wherein said temperature and said pressure are maintained within said vessel over a period from about 3 months to about 4 months.

5. The method of claim 1 wherein said material additionally comprises an anti-bacterial agent.

6. The method of claim 5 wherein said anti-bacterial agent is selected from the group consisting of streptomycin, chloromycetin, penicillin, and mixtures thereof.

7. The method of claim 2 wherein the selected tissue is fresh human placenta.

8. The method of claim 7 wherein air is removed from said vessel and a gas providing a reducing atmosphere introduced in lieu thereof.

9. The method of claim 8 wherein the recovery step (e) comprising adjusting the pH of said contents to a pH from about 7.3 to about 7.4 and boiling said contents to coagulate contained liquid, heat-unstable protein.

10. The method of claim 1 wherein air is removed from said vessel and a gas providing a reducing atmosphere introduced in lieu thereof.

* * * * *